United States Patent
Page

(10) Patent No.: US 8,721,654 B2
(45) Date of Patent: May 13, 2014

(54) OPTHALMIC LENS CAPSULE SUPPORT

(75) Inventor: Timothy Patrick Page, Birmingham, MI (US)

(73) Assignee: William Beaumont Hospital, Royal Oak, MI (US)

( * ) Notice: Subject to any disclaimer, the term of this patent is extended or adjusted under 35 U.S.C. 154(b) by 57 days.

(21) Appl. No.: 13/055,732

(22) PCT Filed: Jul. 24, 2009

(86) PCT No.: PCT/US2009/051707
§ 371 (c)(1),
(2), (4) Date: Apr. 7, 2011

(87) PCT Pub. No.: WO2010/011936
PCT Pub. Date: Jan. 28, 2010

(65) Prior Publication Data
US 2011/0178527 A1    Jul. 21, 2011

Related U.S. Application Data

(60) Provisional application No. 61/083,737, filed on Jul. 25, 2008.

(51) Int. Cl.
*A61F 9/00* (2006.01)
(52) U.S. Cl.
USPC .......................................... 606/107; 606/114
(58) Field of Classification Search
USPC ......... 606/107, 110, 113, 114, 127, 128, 161, 606/162; 623/6.12
See application file for complete search history.

(56) References Cited

U.S. PATENT DOCUMENTS

| | | | |
|---|---|---|---|
| 4,619,657 A | 10/1986 | Keates et al. | |
| 4,692,142 A | 9/1987 | Dignam et al. | |
| 5,123,906 A | 6/1992 | Kelman | |
| 5,201,741 A | 4/1993 | Dulebohn | |
| 5,279,554 A | 1/1994 | Turley | |
| 5,476,512 A | 12/1995 | Sarfarazi | |
| 5,581,890 A | 12/1996 | Schmidt | |
| 5,676,669 A | 10/1997 | Colvard | |
| 5,873,879 A | 2/1999 | Figueroa et al. | |
| 5,890,290 A | 4/1999 | Davis | |
| 5,891,153 A * | 4/1999 | Peterson | 606/107 |
| 6,146,388 A | 11/2000 | McDonald | |
| 6,183,480 B1 | 2/2001 | Mackool | |
| 6,245,078 B1 | 6/2001 | Ouchi | |
| 6,371,960 B2 | 4/2002 | Heyman et al. | |
| 6,387,101 B1 | 5/2002 | Butts et al. | |
| 6,551,291 B1 | 4/2003 | de Juan, Jr. et al. | |

(Continued)

OTHER PUBLICATIONS

PCT/EP2009/051707—International Search Report—Sep. 17, 2009.

(Continued)

*Primary Examiner* — Thomas McEvoy
(74) *Attorney, Agent, or Firm* — Honigman Miller Schwarz and Cohn LLP; Douglas H. Siegel; Jonthan P. O'Brien

(57) ABSTRACT

A lens support system for use during extracapsular cataract surgery. The lens support system may be used to support a lens or lens fragment in the event of a posterior capsule tear or zonular dialysis. The lens support system comprises a cannula in which a piston attached to a lens support is slidably disposed. By means of the piston, the lens support is movable between collapsed and expanded configurations.

9 Claims, 8 Drawing Sheets

(56) References Cited

U.S. PATENT DOCUMENTS

| | | |
|---|---|---|
| 6,554,843 B1 | 4/2003 | Ou |
| 6,558,395 B2 | 5/2003 | Hjertman et al. |
| 6,561,974 B1 | 5/2003 | Grieshaber et al. |
| 6,921,405 B2 | 7/2005 | Feingold et al. |
| 6,936,053 B1 | 8/2005 | Weiss |
| 6,976,989 B1 | 12/2005 | Vincent |
| 7,147,644 B2 | 12/2006 | Weber et al. |
| 7,186,258 B2 | 3/2007 | Sabet |
| 7,229,476 B2 | 6/2007 | Azar |
| 2002/0091306 A1 | 7/2002 | De Juan, Jr. et al. |
| 2004/0153093 A1* | 8/2004 | Donovan .............. 606/108 |
| 2008/0021399 A1 | 1/2008 | Spaide |

OTHER PUBLICATIONS

Y.M. Por, M.J. Lavin, "Techniques of Intraocular Lens Suspension in the Absence of Capsular/Zonular Support," Survey of Opthamaology, Sep. 2005 (vol. 50, Iss. 5, pp. 429-462).

European Search Report—Jul. 10, 2011.

\* cited by examiner

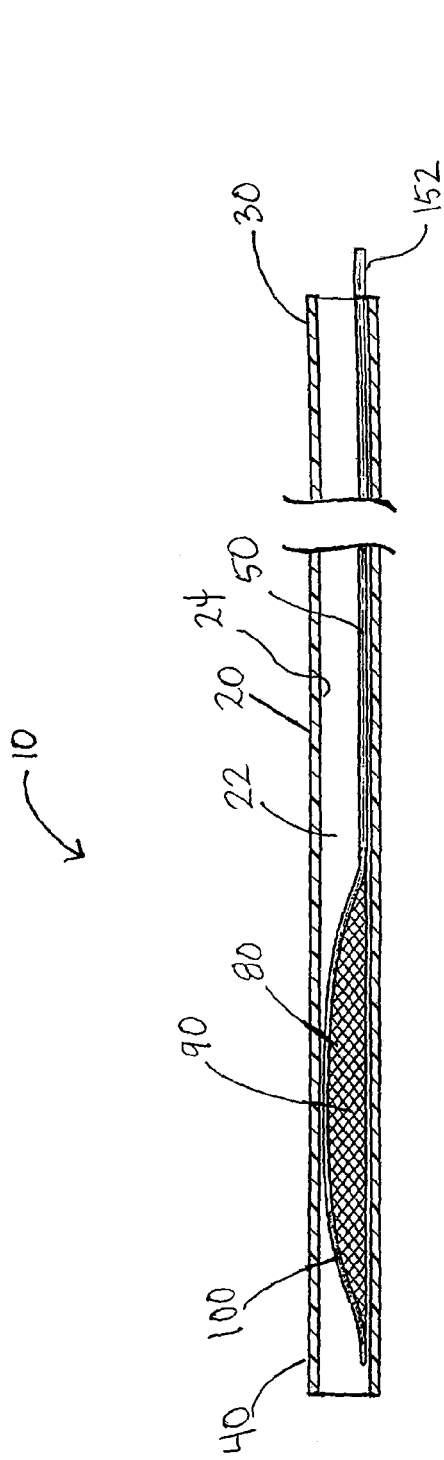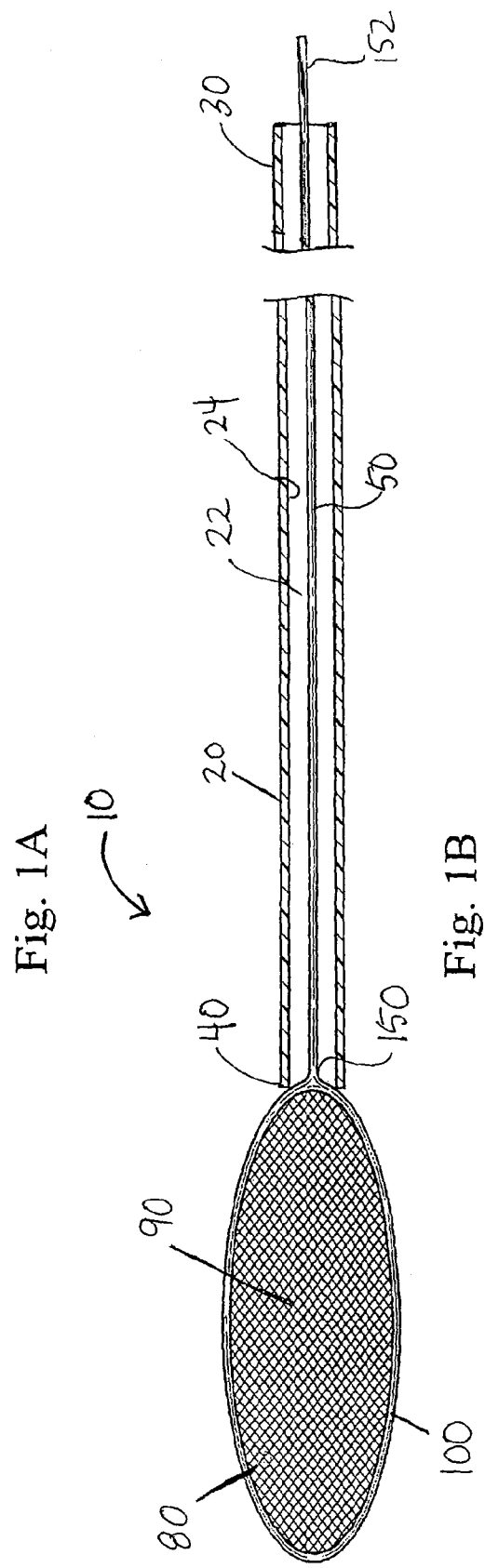
Fig. 1A
Fig. 1B

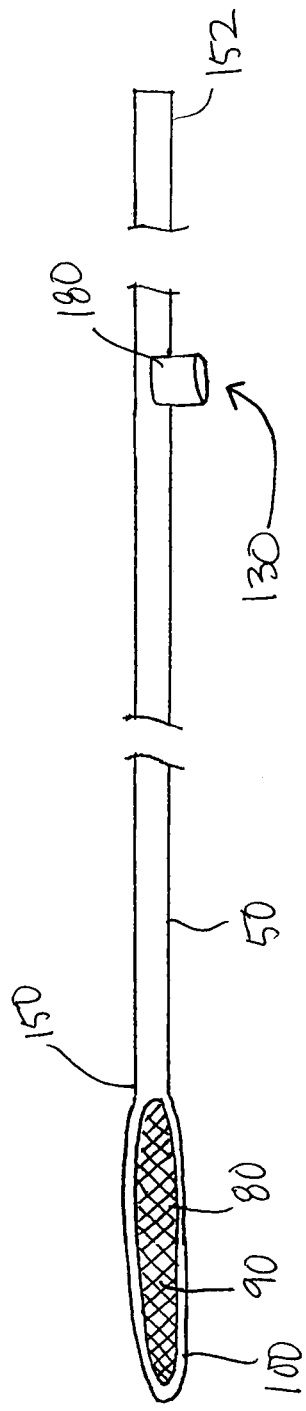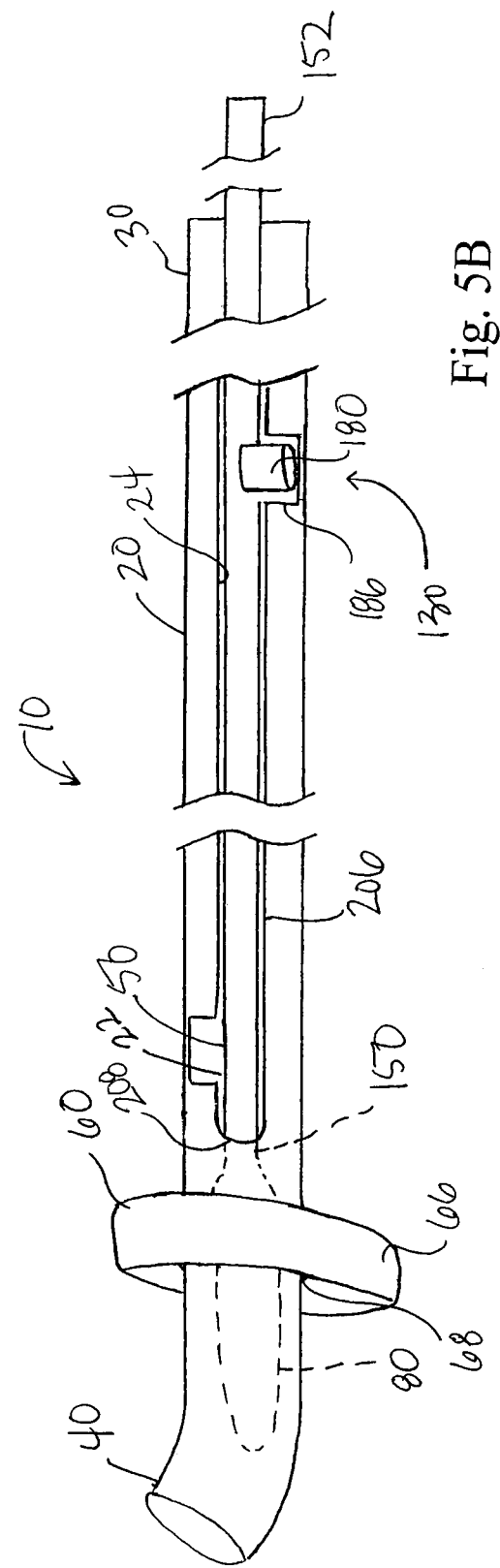

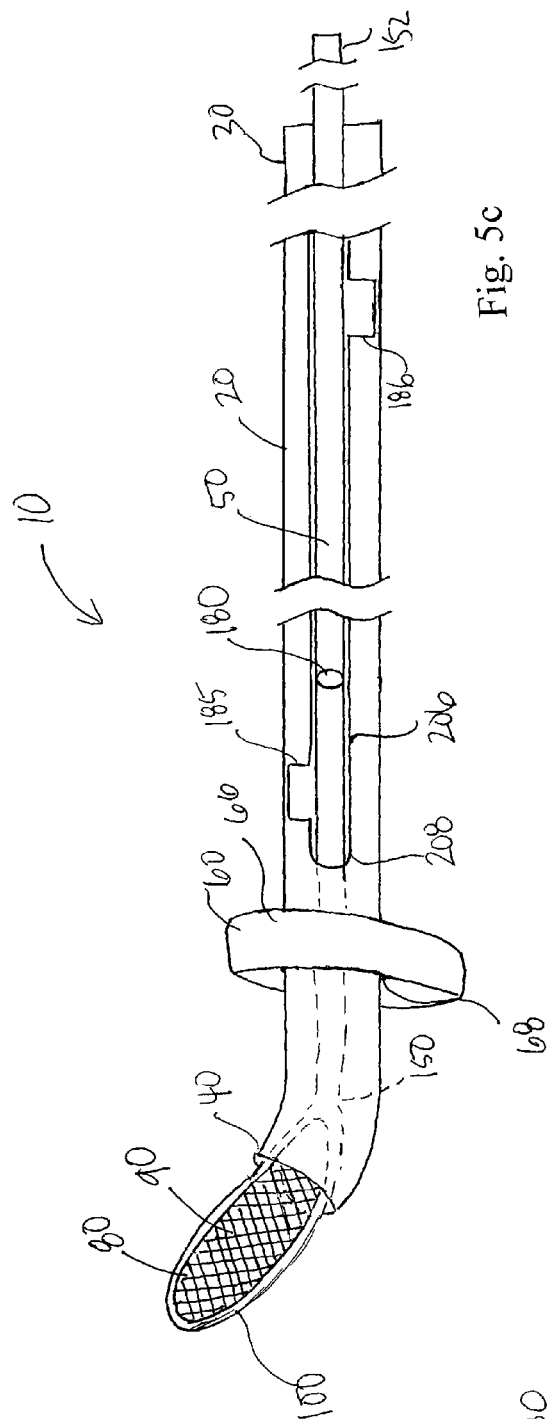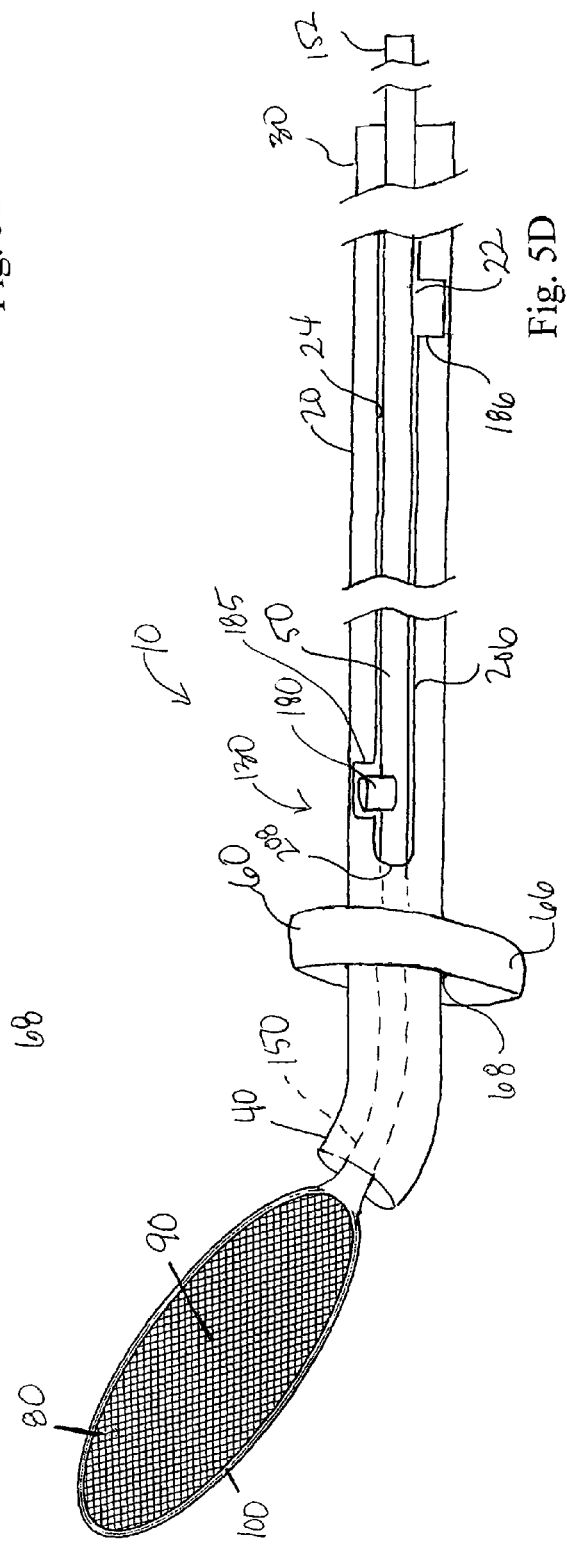

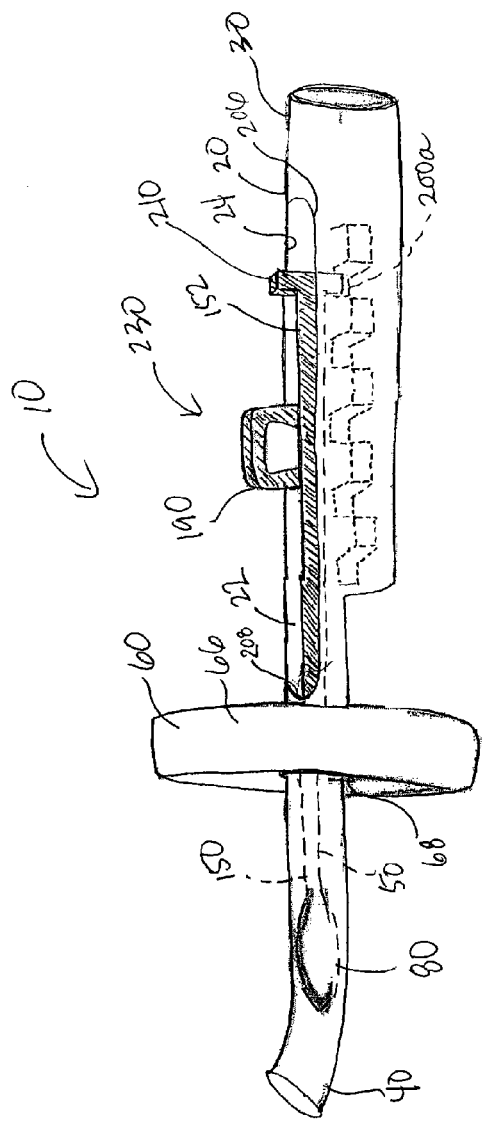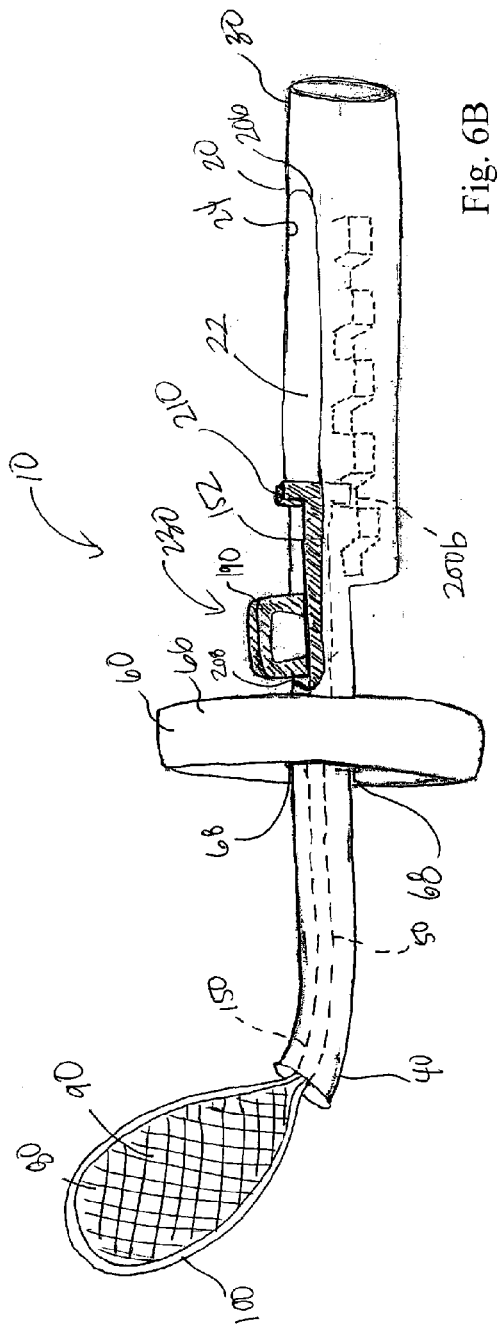

OPTHALMIC LENS CAPSULE SUPPORT

CROSS REFERENCE TO RELATED APPLICATIONS

This application claims priority to U.S. Provisional Patent Application No. 61/083,737, filed Jul. 25, 2008 and PCT/US2009/051707, Filed Jul. 24, 2009.

BACKGROUND OF THE INVENTION

Cataract surgery has greatly improved in over the past 40 years. In the early cataract surgeries, the primary method for the removal of the cataract was by intracapsular cataract extraction. This method involves the removal of the entire lens structure including the capsular bag. While this method, in conjunction with the use of special glasses or contacts, was typically effective in restoring vision, removal of the capsular bag allowed the vitreous body to move forward into the anterior area of the eye. This movement of the vitreous body can lead to postoperative complications such as retinal detachment, glaucoma, corneal decompensation and uveitis.

The introduction of microscopes to cataract surgery has allowed surgeons to improve their techniques. It is now standard to remove the nucleus and cortical material through a small incision in the anterior capsule while leaving the posterior capsule in place. This technique is referred to as extracapsular cataract surgery. Because the posterior capsule is left intact, it can help to support the vitreous body and prevent it from moving forward into the anterior portion of the eye.

Extracapsular cataract surgery significantly reduces intraoperative as well as post operative complications of cataract surgery compared to rates seen with intracapsular cataract extraction. However, complications including posterior capsule tear, zonular dialysis and intraocular lens (IOL) subluxation, can occur. In the presence of a posterior capsule tear, nuclear material and posterior chamber IOLs may subluxate intraoperatively or postoperatively into the vitreous body which may lead to many of the same complications associated with intracapsular cataract surgery. Removal of the nuclear material from the vitreous may be difficult and it involves an additional procedure called a vitrectomy. Even if all the nuclear material is removed by the vitrectomy, there is an increased risk of retinal complications.

In addition to the possibility of a posterior capsule tear, there is a risk of intraoperative traumatic zonular dialysis. The zonule fibers provide support for the lens capsule. Compromise of the zonule fibers during surgery may allow the lens capsule to subluxate into the vitreous which may lead to complications. A lens may also sublux spontaneously due to zonular dialysis from a number of metabolic and ocular conditions including trauma.

A technique to capture nuclear fragments and prevent their migration through a posterior capsule tear has been described in U.S. Pat. No. 7,186,258. A net is mechanically constrained by a device and is inserted while in the constrained configuration into the lens capsule through a small incision into the lens capsule. The net is then allowed to expand behind the nucleus. After removal of the nuclear fragments the net may be withdrawn into the device and withdrawn from the eye in the contracted configuration. This technique is not ideal because it may block removal of nuclear fragments that are between the net and the posterior capsule or nuclear fragments that have partially migrated into the vitreous body.

A technique known as posterior assisted levitation (POL) has been used to elevate nuclear fragments that have descended behind the posterior capsule because of intraoperative posterior capsule tear in order to facilitate their removal. In addition, this technique has been used to elevate subluxated lens capsules. POL generally involves insertion of a probe through the pars plana and positioning the probe behind the nuclear fragment. The tip of the probe is then elevated to bring the fragment into the anterior chamber. The probe is sometimes referred to a spatula. However, because of the small diameter of the probe, approximately 0.5-0.8 mm, balancing and elevating the nuclear fragments on the probe is technically difficult even in the hands of experienced cataract surgeons.

While the rate of complications associated with cataract surgery is low, some reports estimate the percent of complications involving the posterior capsule to be in the range of 0.5% to 5.0% and the occurrence of lens dislocation to be between 0.2% and 1.8%. Given these numbers, there is a need for additional improved techniques that can prevent complications resulting from cataract surgery.

BRIEF SUMMARY OF THE INVENTION

The present invention provides a hands-free lens support system for use in supporting the crystalline lens, lens capsule, lens fragments, or subluxed pseudophakic lenses during extracapsular cataract surgery after a posterior capsule tear or zonular dialysis.

The lens support system may be used during cataract surgery in which various techniques are used for removal of the nucleus, including but not limited to intracapsular cataract extraction, extracapsular cataract with nuclear expression, and extracapsular cataract extraction with phacoemulsificaton. Particularly contemplated is the use of phacoemulsification. The lens support system may also be used to support a crystalline or pseudophakic lens prior to surgery in which loose or detached zonules have been identified by way of phacodonesis, subluxation, or B scan ultrasonography of the posterior capsule in traumatic cataracts.

In the case of a posterior capsule tear, the lens support is typically used intraoperatively after a posterior capsule tear has occurred, or preoperatively in traumatic cataracts with a known rupture of the posterior capsule. In the case of zonular dialysis, the lens support is typically used intraoperatively after a large zonular dialysis has been identified. In certain circumstances in which the patient is known to be at risk for the occurrence of zonular dialysis, for example patients having suffered ocular trauma, or having pseudoexfoliation syndrome, Marfan syndrome, cystinosis, high myopia, or Ehler-Danlos syndrome, the lens support may be used prophylactically before lens fragmentation. This prophylactic use may aid in continuous curvilinear capsulorhexis and/or reduce of the risk of posterior displacement of lens fragments or IOL during surgery, avoiding further vitrectomy surgery at another date.

The lens support system of the present invention generally includes a cannula, a piston movable within the passage or lumen of the cannula, a lens support connected to a distal portion of the piston, a fixation device, and a stop. The lens support system allows the precise and controlled placement of a lens support between the posterior capsule and the vitreous body to prevent nuclear fragments from moving into the vitreous body after a posterior capsule tear or to provide support for the lens in the event of zonular dialysis. Once the lens support is placed in the desired position, the fixation device, in combination with the stop, retains the lens support in position, allowing hands-free use of the lens support system.

In one embodiment of the present invention, the lens support system includes a cannula with a tubular wall having a proximal end and a distal end and defining a lumen formed therethrough. A piston including a proximal portion and a distal portion is slidably disposed within the lumen of the cannula. Attached to the distal portion of the piston, is a lens support which is movable with the piston. The lens support includes an expandable frame defining an opening. A membrane is attached to the frame to span the opening thereof. The lens support is movable between a collapsed configuration and an expanded configuration. A fixation device is positioned about a distal portion of the cannula and cooperable therewith to maintain the cannula in a fixed position relative to the eye. A stop is positioned a predetermined distance from the lens support and cooperable with the cannula and the piston to maintain the piston in a fixed position.

In another example, the present invention provides a method of supporting a lens of a patient's eye. The method includes cutting an incision in a pars plana of the eye and inserting a lens support through the incision to position the lens support within the patient's eye adjacent the lens, between the posterior capsule and the vitreous body of the eye. The lens support includes an expandable frame and a membrane attached to the frame. The frame is attached to a piston at a distal end thereof. The piston is slidably disposed within a lumen of a cannula. The lens support is movable with the piston between a collapsed configuration and an expanded configuration. In this embodiment, inserting the lens support includes inserting the cannula through the incision in the pars plana with the lens support housed within the lumen of the cannula in the collapsed configuration. The step of inserting the lens support further includes positioning a fixation device about the cannula and adjacent the incision outside the eye to maintain the cannula in a fixed position and advancing the piston within the lumen of the cannula toward a distal end thereof to deploy the lens support to the expanded configuration to support the lens.

Further aspects, features, and advantages of the invention will become apparent from consideration of the following description and the appended claims when taken in connection with the accompanying drawings.

BRIEF DESCRIPTION OF THE DRAWINGS

FIG. 1A is a side cross-sectional view of a lens support system, shown with the piston in a retracted position and the lens support constrained in a contracted configuration within the cannula;

FIG. 1B is a side cross-sectional view of a lens support system, shown with the piston in an advanced position and the lens support in an expanded configuration outside the cannula;

FIG. 5A is a side perspective view of a piston of a lens support system in accordance with an embodiment of the present invention, the piston shown with a locking attachment attached thereto;

FIG. 5B is a side perspective view of a lens support system in accordance with an embodiment of the present invention, shown with the locking attachment of the piston of FIG. 5A in an engaged position and the lens support in a contracted configuration;

FIG. 5C is a side perspective view of the lens support system of FIG. 5B, shown with the locking attachment in a disengaged position;

FIG. 5D is a side perspective view of the lens support system of FIG. 5B, shown with the locking attachment in an engaged position and the lens support in an expanded configuration;

FIG. 6A is a side perspective view of a lens support system in accordance with yet another embodiment of the present invention including a stop having a slider and a tab connected to a piston, shown with the tab engaged with a proximal cog;

FIG. 6B is a side perspective view of the lens support system of FIG. 6A, shown with the tab engaged with a distal cog.

DETAILED DESCRIPTION OF THE INVENTION

Figure 2:
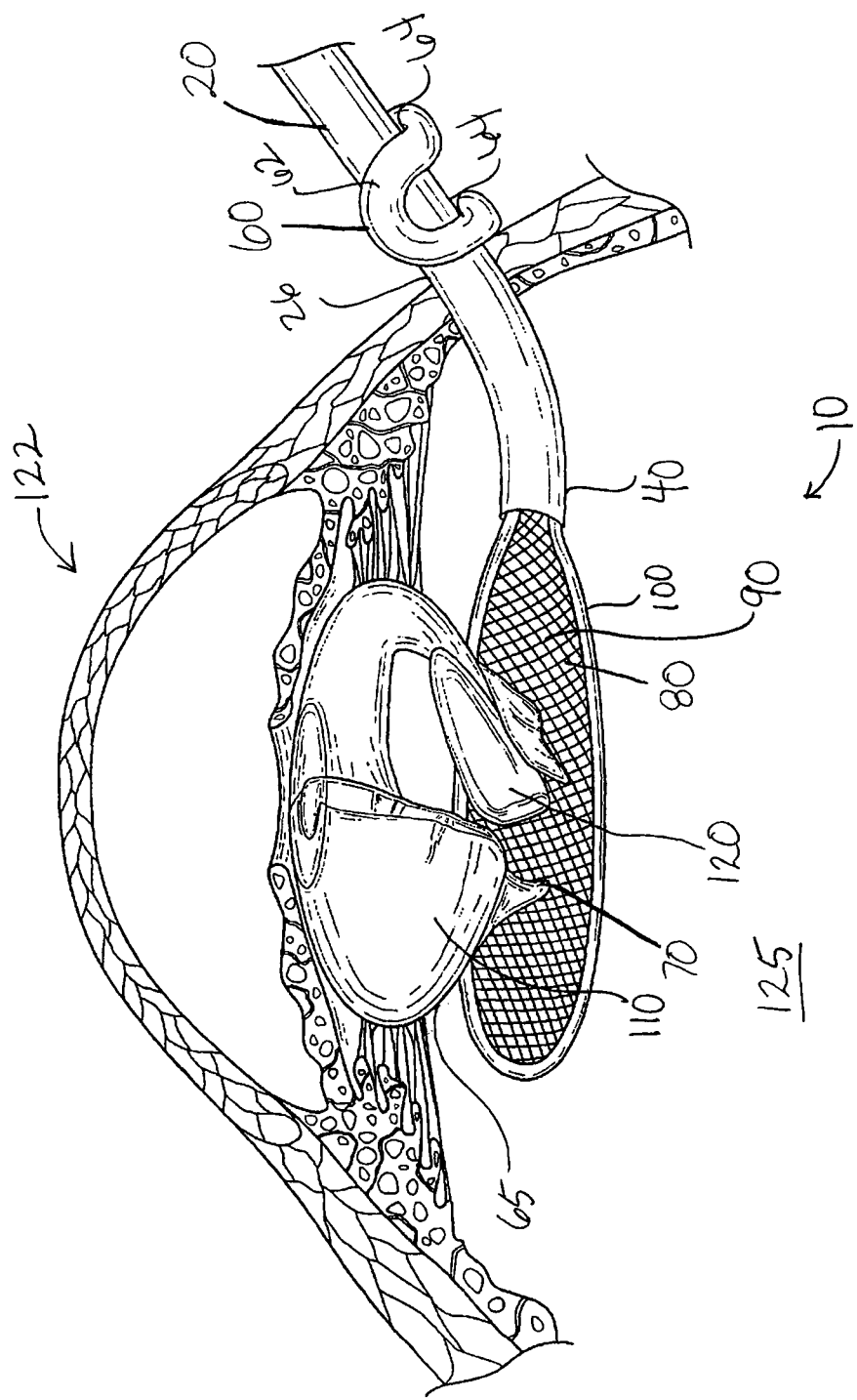
FIG. 2 is a perspective view of a lens fragment descending through a posterior capsule tear and a lens support system in accordance with an embodiment of the present invention supporting the lens fragment.

The term "lens" includes but is not limited to, crystalline lens, intraocular lens, and pseudophakic lens.

The terms "lens fragments" and "nuclear fragments" are used interchangeably.

The term "proximal" refers to an end of the device or system which in use is closest to the physician during the medical procedure and the term "distal" refers to an end of the device or system which in use is furthest from the physician during the medical procedure, including within the patient.

The embodiments below are described with reference to the drawings in which like elements are referred to with like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not drawn to scale and, in certain instances, details which are not necessary for an understanding of the embodiments have been omitted.

Various embodiments of the lens support system 10 according to the present invention are illustrated in FIGS. 1-6. The lens support system 10 generally includes a cannula 20 open at a proximal end 30 and a distal end 40, a piston 50 movable within a lumen 22 of the cannula 20, a lens support 80 connected to the piston 50, a fixation device 60, and a stop 130.

Referring to FIGS. 1A and 1B, the lens support system 10 includes a cannula 20 having a proximal end 30 and a distal end 40. The cannula 20 has a tubular wall 24 having proximal and distal ends 40, 30 and defining a lumen 22 formed therethrough. A piston 50 is slidably disposed within the lumen 22 of the cannula 20 and a lens support 80 is attached to the distal end 150 of the piston 50. The lens support 80 includes a membrane 90 which is attached to and supported by a frame 100. In FIG. 1A, the piston 50 is in a retracted configuration and the lens support 80 is housed within the lumen 22 of the cannula 20, wherein the constraining force of the cannula tubular wall 24 maintains the lens support 80 in a contracted or collapsed configuration. FIG. 1B shows the piston 50 in an advanced position and the lens support 80 deployed from the distal end 40 of the cannula 20, wherein the lens support 80 is free from the constraining force of the cannula tubular wall 24 and biased to an expanded configuration.

In this embodiment, the cannula 20 has a diameter that permits introduction of the lens support 80 through a small incision, preferably between about 1 mm and about 2 mm, in the pars plana of the eye 122. Preferably, the cannula 20 has a diameter of between about 0.4 mm and 0.6 mm. Preferably, the diameter of the cannula 20 is of a size that allows for a sutureless surgery. The cannula 20 may be formed from any suitable flexible material known by one of skill in the art including but not limited to polytetrafluoroethylene.

In this embodiment, the frame 100 defines a smaller first diameter in the collapsed configuration and a larger second diameter in the expanded configuration. In the expanded configuration, the frame 100 is sized to support the lens 110 or lens fragments 120 and prevent migration of the lens 110, lens capsule 115, or lens fragments 120 into the vitreous body 125. Preferably, the frame 100 expands to a diameter of between about 0.8 cm and about 1.6 cm. The frame 100 preferably includes a predetermined curved shape in the expanded configuration which corresponds substantially to the anatomical curvature of the lens 110.

As shown in FIG. 1B, the frame 100 preferably defines an ovular perimeter defining an opening spanned by the membrane 90. The membrane 90 is attached to the frame 100 by any suitable means known by one of skill in the art including but not limited to adhesive bonding. The frame 100 is attached to the distal end 150 of the piston 50 by any suitable means known by one of skill in the art including but not limited to soldering, laser welding, or adhesive bonding. Alternatively, the frame 100 may be formed integrally with the piston 50 as a single piece.

Preferably, the frame 100 is made of any suitable material that is capable of being compressed within the cannula 20 and when extended from the cannula 20 is capable of self-expanding by its own elasticity to provide a sufficient outward bias to support the lens 110, lens capsule 115, or lens fragments 120 in the expanded configuration. The material may be, for example, a shape memory material including but not limited to superelastic materials, stainless steel, cobalt-chromium-nickel-molybdenum-iron alloy, cobalt-chrome alloy, or nickel titanium alloy, more commonly known as nitinol. Preferably, the membrane 90 is made of any biocompatible material, for example, a plastic or metal that is compatible with extracapsular cataract surgery and which allows for movement of the membrane 90 between the contracted and expanded configurations. Suitable materials include, for example, Nylon, Dacron, Thorolon, polyethylene, silicon, or any of the materials listed above with respect to the frame 100.

As illustrated in FIGS. 1A and 1B, movement of the piston 50 toward the distal end 40 of the cannula 20 advances the lens support 80 from the cannula 20 and the lens support 80 self-expands to the expanded deployed configuration. Retraction of the piston 50 towards the proximal end 30 of the cannula 20 draws the lens support 80 back within the cannula 20 and into the contracted configuration. When the lens support 80 is retracted into the cannula 20, the frame 100 of the lens support 80 is compressed due the constraining forces of the cannula tubular wall 24 and the frame 100 and membrane 90 collapse defining the collapsed configuration.

Figure 3:
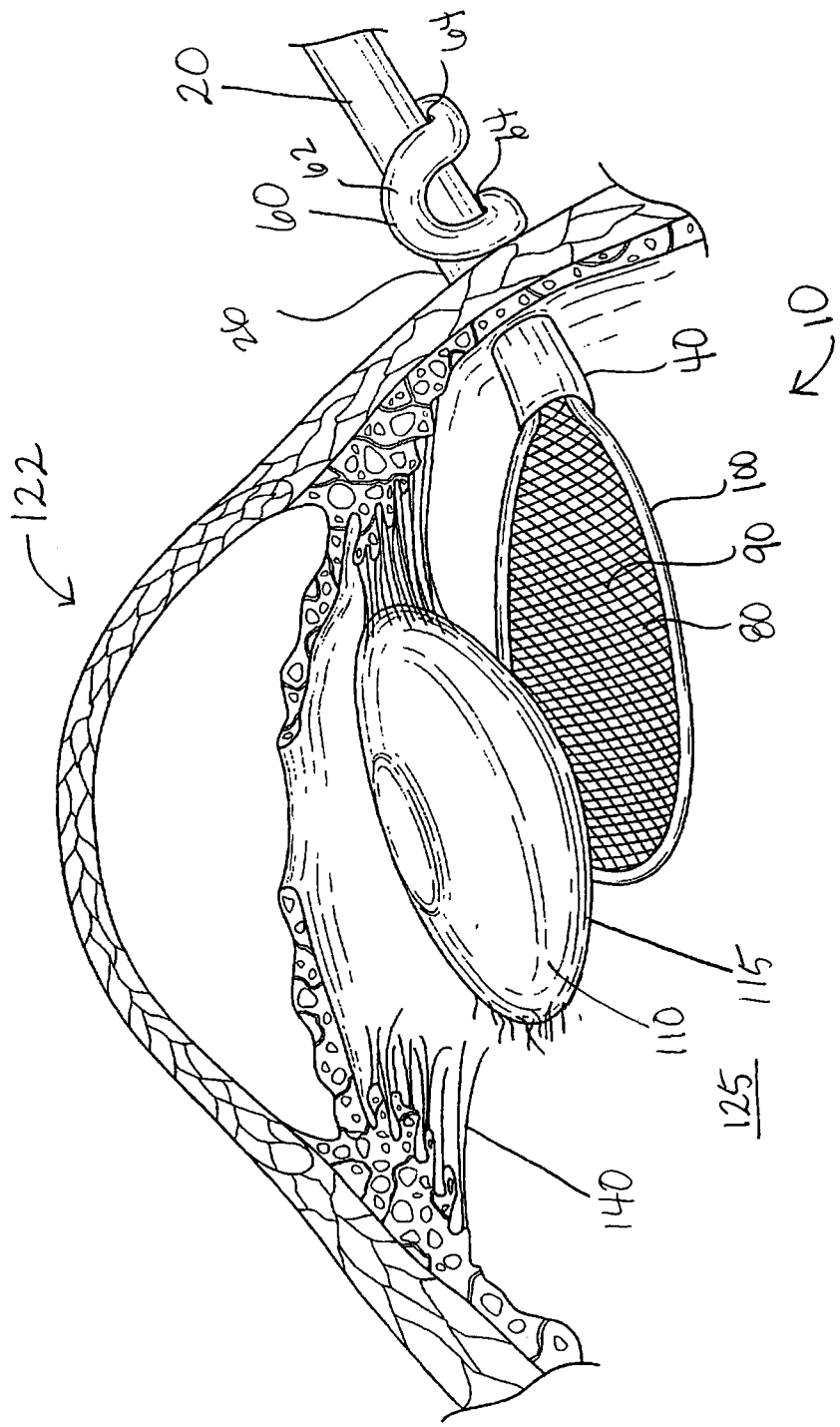
FIG. 3 is a perspective view of a lens capsule descending into the vitreous body following zonular dialysis and a lens support system in accordance with an embodiment of the present invention supporting the lens capsule.
Figure 4:
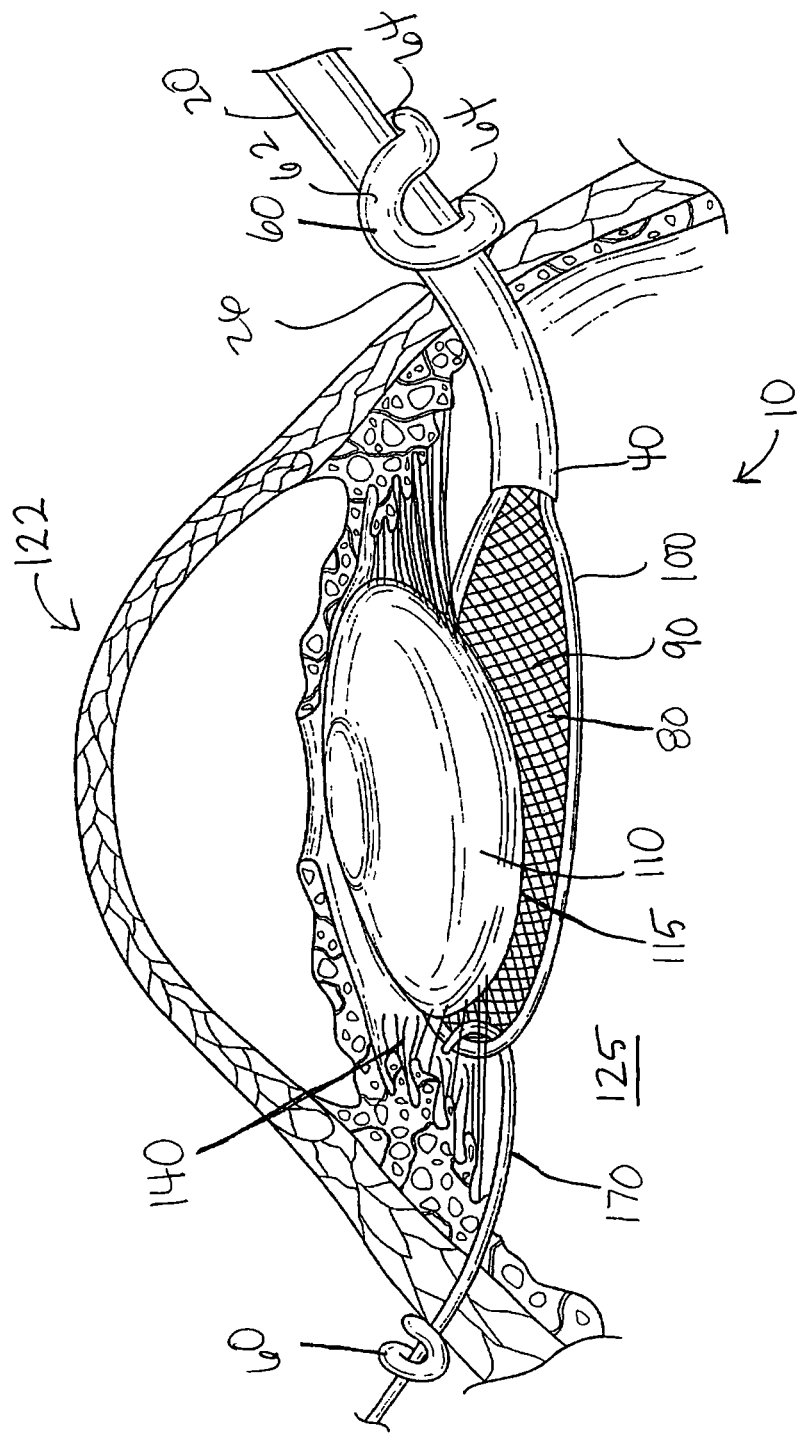
FIG. 4 is a perspective view of a lens capsule supported by a lens support system and a hook in accordance with another embodiment of the present invention.

FIG. 2 illustrates the lens support system 10 supporting a lens fragment 120 which is descending through a posterior capsule tear 70. The fixation device 60 maintains the cannula 20 in a fixed position which directs the position of the lens support 80 between the posterior capsule 65 and the vitreous body 125. FIG. 3. Illustrates the lens support system 10 supporting a lens capsule 115 which has partially descended into the vitreous body 125 after zonular dialysis 140. The fixation device 60 maintains the cannula 20 in a fixed position which directs the position of the lens support 80 posterior to the lens capsule 115. FIG. 4 illustrates the lens support system 10, in combination with a hook 170, supporting a lens capsule 115 after zonular dialysis 140.

As shown in FIGS. 2-4, the fixation device 60 is a disk including a body 62 and two holes 64 formed therethrough, each of which receives a distal portion 26 of the cannula 20, preferably forming a friction fit with the cannula 20. In this embodiment, the disk 60 is preferably flexed into a crescent shape such that the holes 64 are in alignment to consecutively receive the cannula therethrough. The disk 60 is movable along the tubular wall 24 of the cannula 20. Once the cannula 20 is inserted at the desired position within the eye 122, the disk 60 is slid toward the distal end 40 of the cannula 20 to fit snugly against an outer surface of the eye 122 near the incision cut through the pars plana, thus fixing the cannula 20 in a fixed position. Before the cannula 20 is removed, the disk 60 is slid toward the proximal end 30 of the cannula 20.

In other embodiments, such as those illustrated in FIGS. 5B, 5C, 6A, and 6B, the fixation device 60 may be a flexible washer or flange which receives the cannula 20. In this embodiment, the flange includes a ring 66 having an opening 68 formed therethrough to receive the cannula 20. Once the cannula 20 is inserted at the desired position in the eye 122, the flange 60, which preferably forms a friction fit with the cannula 20, is slid toward the distal end 40 of the cannula 20 to fit snugly against an outer surface of the eye 122 near the incision cut through the pars plana, thus fixing the cannula 20 in a fixed position. Before the cannula 20 is removed, the flange 60 is slid toward the proximal end 30 of the cannula 20.

In other embodiments of the present invention, the fixation device 60 may include a disk having a hole in the center that is inserted into an incision in the sclera. After the disk is fixed in the sclera, the cannula 20 is slid, using moderate intentional force, through the hole in the disk. The disk is configured such that there is sufficient resistance between the fixation device 60 and the cannula 20 to maintain the cannula 20 in a fixed location in the absence of the moderate intentional force. The disk, when inserted into the sclera, is held in place by virtue of the elasticity of the sclera. The cannula 20 can likewise be withdrawn from the fixation device 60 with moderate intentional force and the disk subsequently removed. One example of a suitable disk is a metal trocar, such as that commonly used in sutureless 25 and 23 gauge vitrectomy surgery.

The fixation device 60 serves to hold the cannula 20 in place after insertion through the incision in the pars plana and can be designed in many ways and may include devices used in other surgical or medical instruments. The fixation device 60 allows for the movement of the cannula 20 using moderate intentional force, yet the fixation device 60 has sufficient resistance to prevent unintentional movement of the cannula 20. The fixation device 60 may be made of any biocompatible material, including but not limited to silicon rubber, and may be formed of any shape such that the fixation device 60 is capable of securing the cannula 20 in place relative to the eye 122. One skilled in the art would be able to identify suitable devices including but not limited to devices that are currently used in surgical procedures or modifications of known devices.

As provided above, the lens support 80 is fixed to the distal end 150 of the piston 50 and the piston 50 is manipulated to move the lens support 80 distally or proximally within the lumen 22 of the cannula 20. Thus, the position of the piston 50 controls the degree of expansion of the lens support 80.

Movement of the piston 50 may be by direct manipulation of the piston 50, i.e., manual manipulation of the proximal end 152 of the piston 50 extending beyond the proximal end 30 of the cannula 20, or by indirect manipulation.

When the piston 50 is positioned such that the lens support 80 is entirely disposed within the cannula 20, the lens support 80 is constrained in a contracted collapsed configuration. When the piston 50 is advanced such that the lens support 80 is fully outside the cannula 20, the lens support 80 is in a fully expanded deployed configuration. The piston 50 may be positioned such that less than the entire lens support 80 is outside the cannula 20. The degree of advancement of the lens support 80 outside the cannula 20 controls the degree of expansion of the lens support 80. One skilled in the art would be able to identify the appropriate degree of expansion of the lens support 80 for addressing various conditions that may occur during extracapsular cataract surgery. For example, the lens support 80 may be used in a less than fully expanded configuration, or partially deployed configuration, when one or more nuclear fragments remain after removal of the lens 110 and such fragments are in a position to be supported with a less than fully expanded lens support 80, using the device as one would use a posterior levitation technique with a probe, but with an expanded support to prevent posterior displacement of the lens fragment.

As stated previously, the piston 50 may be movable within the lumen 22 of the cannula 20 by direct manipulation of the piston 50. Alternatively, referring to FIGS. 5A-C and 6A-B, the piston 50 may be movable within the lumen 22 of the cannula 20 through manipulation of a stop 130, wherein the position of the piston 50 relative to the cannula 20 is controlled by the stop 130. The stop 130 may comprise any mechanism that allows the piston 50 to be manipulated into the desired position and to retain the piston 50 in that position. The stop 130 is positioned a predetermined distance from the lens support 80 such that it is capable of controlling the movement of the piston 50 relative to the cannula 20 to maintain the lens support 80 in one of the collapsed or deployed configurations. One skilled in the art would be able to identify suitable mechanisms including but not limited to mechanisms that are currently used in surgical procedures or modifications of these devices.

As illustrated in FIGS. 5A-D, the lens support system 10 includes a stop 130 having a knob or locking attachment 180 fixed to the piston 50. The piston 50 is movable within a slot 206 formed in the tubular wall 24 of the cannula 20. The piston 50 can be rotated to engage the locking attachment 180 in a proximal notch 186 in the cannula 20 which fixes the piston position such that the lens support 80 is in a contracted configuration. The locking attachment 180 can also be rotated and the piston 50 advanced to engage the locking attachment 180 in a distal notch 185 which fixes the piston position such that the lens support 80 is in an expanded configuration. When the piston is rotated such that the locking attachment 180 is disengaged, the piston 50 is freely movable within the cannula 20 and therefore is able to advance or retract the lens support 80.

FIG. 5A shows the locking attachment 180 fixed to the piston 50. FIG. 5B shows the locking attachment 180 engaged in the proximal notch 186, wherein the piston 50 is in the retracted position and the lens support 80 is in the contracted collapsed configuration. FIG. 5C shows the locking attachment 180 in a disengaged position and the piston 50 being distally advanced toward the distal end 40 of the cannula 20 to deploy the lens support 80, the lens support 80 being shown in a partially deployed or partially expanded configuration. FIG. 5D shows the locking attachment 180 engaged in the distal notch 185, wherein the piston 50 is in an advanced position and the lens support 80 is in the deployed or expanded configuration. In this embodiment, the locking attachment 180 is attached to the piston 50 at a predetermined distance from the lens support 80 attached at the distal end 150 thereof such that when the locking attachment 180 engages the distal edge 208 of the slot 206 formed in the wall 24 of the cannula 20 the lens support 80 is in the deployed expanded configuration and capable of freely moving in the deployed configuration for proper positioning of the lens support 80 relative to the lens 110, lens capsule 115, or lens fragments 120.

FIGS. 6A and 6B illustrate a further embodiment of a lens support system 10 the present invention in which the stop 230 comprises a slider 190 movable within in a slot 206 formed in the tubular wall 24 of the cannula 20. The slider 190 is attached to the piston 50 along the proximal portion 152. The piston 50 includes a lever or tab 210 located proximally from the slider 190. The tab 210 cooperates with cogs 200 to lock the piston 50 in position and thereby limit the movement thereof. As illustrated in FIG. 6a, the tab 210 is engaged with a proximal cog 200a, locking the piston 50 in a retracted proximal position wherein the lens support 80 is in the collapsed configuration housed within the lumen 22 of the cannula 20. In this embodiment, the slider 190 is depressed and manipulated to disengage the tab 210 from the cogs 200. When the tab 210 is disengaged from the cogs 200, the piston 50 can be easily advanced or retracted by sliding the slider 190 within the slot 206. After advancing the piston 50 to an advanced position to deploy the lens support 80 from the distal end 40 of the cannula, the compression force on the slider 190 is released causing to the tab 210 to engage a distal cog 200b, as shown in FIG. 6B, wherein the piston is in an advanced distal position and the lens support is in the expanded deployed configuration.

In this embodiment, the slider 190 and the tab 210 are attached to the piston 50 at a predetermined distance from the lens support 80 attached at the distal end 150 thereof such that when the slider 190 engages the distal edge 208 of the slot 206 formed in the wall 24 of the cannula 20 the lens support 80 is in the deployed expanded configuration and capable of freely moving in the deployed configuration for proper positioning of the lens support 80 relative to the lens 110, lens capsule 115, or lens fragments 120. Likewise, the cogs 200 are disposed within the cannula 20 at a predetermined position such the lens support 80 is maintained in the collapsed configuration when the tab 210 engages with the proximal cog 200a and such that the lens support 80 is deployed to the expanded configuration when the tab 210 engages with the distal cog 200b.

Figure 7:
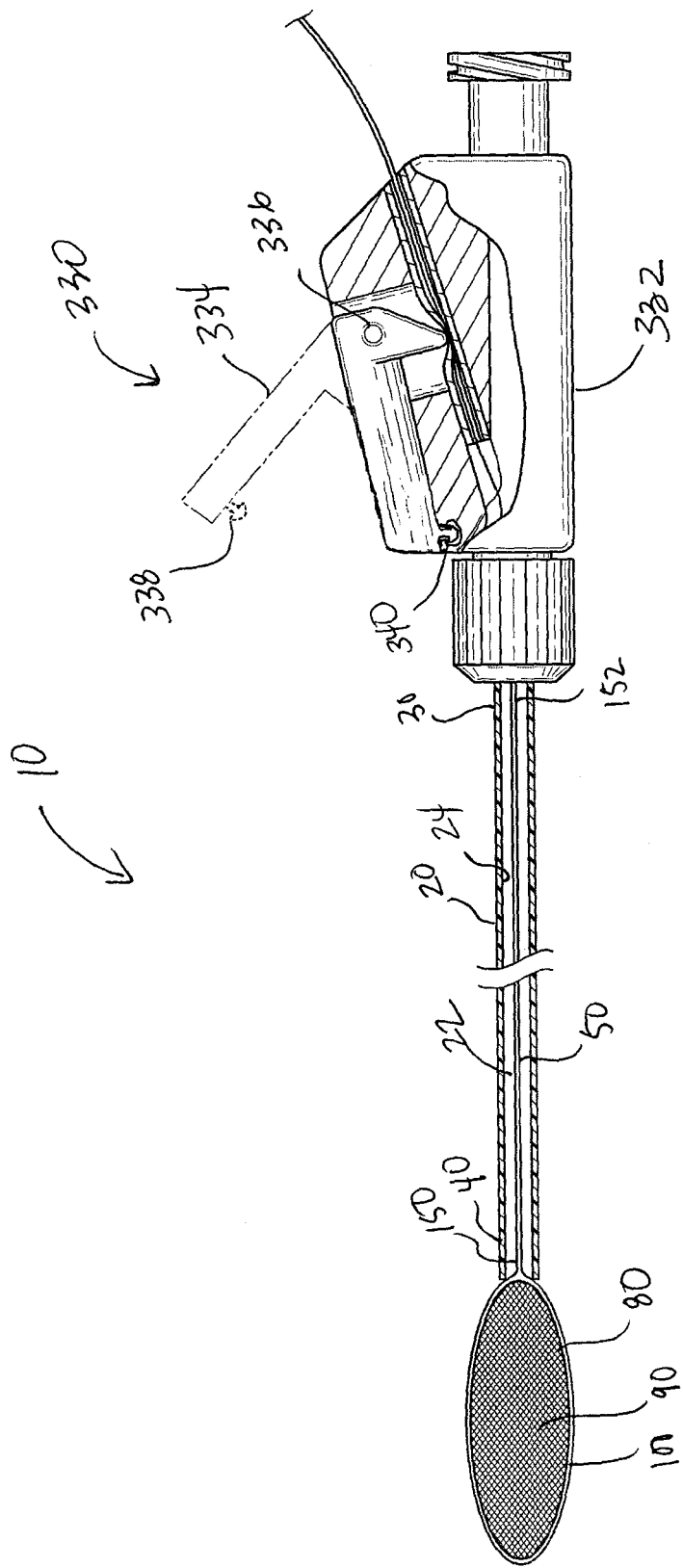
FIG. 7 is a cross-sectional view of a lens support system in yet another embodiment of the present invention.

Referring to FIG. 7, another embodiment of a stop 330 is shown. In this embodiment, the stop 330 includes a hub 332 housing the cannula 20 and the piston 50 disposed therein near their respective proximal ends 30 and 152. Housed within the hub 332, is a lever 334 pivotally mounted on a turning support 336. The lever 334 is movable from an unlocked position (shown in dashed lines) in which the piston 50 is freely slidable within the lumen 22 of the cannula 20 and a locked position (shown in solid lines) in which the pressure-induced lever 334 compresses the tubular wall 24 of the cannula 20 against the piston 50 to prevent movement of the piston 50 within the cannula 20. The lever 334 preferably includes a latch mechanism 338 which cooperates with a recess 340 within the hub 332 to latch the lever in the locked position. To release the stop 330 from the locked position, the lever 334 is unlatched and flipped back into the unlocked position. The latch mechanism 338 may be any suitable mechanism known to one of skill in the art to provide a releasable snap fit to easily move the lever 334 between the unlocked and locked positions to control the fixed positioning of the piston 50.

In another example of a stop, the stop may include a flange or washer which encircles the piston, wherein the stop is of a size to hold the piston securely in place with respect to the cannula yet allows for easy advancement and retraction of the piston. For example, the piston and stop may be similar to that commonly known in the art in typical syringe devices, wherein the friction fit between the stop and the cannula wall substantially fixes the position of the piston within the cannula, and with the application of intentional force allows for easy manipulation of the piston within the cannula.

In certain circumstances it may be desirable to provide additional support to the lens 110 or lens fragments 120 beyond what is provided by the lens support 80 alone. Under these circumstances a second small stab incision is made at a distance from the first incision allowing insertion of a polypropylene hook 170. As illustrated in FIG. 4, the lens support system 10 includes such a hook 170. In this embodiment, the hook 170 is positioned so as to engage the leading edge of the lens support 80. Preferably, the hook 170 is secured with a fixation device 60 so that a desired tension between the hook 170 and lens support 80 is maintained.

In a method of using the lens support system 10 during extracapsular cataract surgery, a small stab incision is made into the pars plana and the lens support 80 is inserted through the incision to position the lens support within the patient's eye 122 whereby, upon expansion of the lens support 80, the lens support 80 is capable of supporting a lens 110, lens capsule 115, or lens fragments 120. The step of inserting the lens support includes partially inserting the cannula 20 through the incision with the lens support 80 housed within the lumen 22 of the cannula 20 in the collapsed configuration. The cannula 20 is secured in a fixed position by sliding a fixation device 60 toward the distal end 40 of the cannula 20 and cinching the fixation device 60 down to an outer surface of the eye 122 adjacent the incision. The piston 50 is then advanced within the lumen 22 of the cannula 20 toward the distal end 40 of the cannula 20 to deploy the lens support 80 to a position behind the posterior capsule and adjacent the lens 110. With the advancement of the piston 50, the lens support 80 self-expands to an expanded configuration.

Preferably, once the lens support 80 is positioned properly within the eye 122, a stop 130 is engaged holding the piston 50 in a fixed position. The lens support 80, in the expanded configuration, supports the lens 110, lens capsule 115, or lens fragments 120 and substantially prevents their movement into the vitreous body 125. Once fragmentation of the lens 110 is complete and the fragments have been removed from the capsule, the stop 130 is disengaged and the piston 50 is retracted, thus drawing the lens support 80 back into the cannula 20 and into the contracted or collapsed configuration and the cannula is withdrawn from within the eye 122.

Those skilled in the art may recognize other equivalents to the specific embodiments described herein. It is to be understood that such changes and variations may be made without departing from scope of the invention. The foregoing description is intended to illustrate and not to limit the scope of the invention, which is defined by the scope of the appended claims.

The invention claimed is:

1. A lens support system for hands-free use in supporting a lens of a patient's eye comprising:
 a cannula having a tubular wall defining a lumen formed therethrough, the tubular wall having a proximal end and a distal end;
 a piston slidably disposed within the lumen of the cannula, the piston including a proximal portion and a distal portion;
 a support attached to the distal portion of the piston and movable therewith configured for placement between a posterior capsule and a vitreous body of the patient's eye, the support including an expandable frame defining an opening and a membrane attached to the frame to span the opening thereof, wherein the support is movable between a collapsed configuration and an expanded configuration;
 a fixation device positioned about a distal portion of the cannula and cooperable therewith to, on its own, maintain the cannula in a fixed position relative to the patient's eye and directs the support between the posterior capsule and the vitreous body; and
 a stop cooperable with the cannula and the piston to maintain the piston in a fixed position relative to the cannula, wherein the stop includes a locking attachment fixed to the piston, wherein the tubular wall of the cannula includes an elongated slot formed therethrough, the slot defining at least one notch, wherein the locking attachment is configured to engage the at least one notch to maintain the piston in a fixed position.

2. The lens support system of claim 1, wherein manipulation of the piston relative to the cannula is configured to move the support between the collapsed configuration and the expanded configuration.

3. The lens support system of claim 1, wherein the fixation device includes a disk having a body and first and second holes formed therethrough, wherein the cannula is received within the first and second holes.

4. The lens support system of claim 1, wherein the fixation device includes a ring having a body and an opening formed therethrough, wherein the cannula is received within the opening.

5. The lens support system of claim 1, wherein the at least one notch defined by the slot includes a proximal notch and a distal notch, wherein the locking attachment is configured to engage the proximal notch to maintain the piston in a retracted position wherein the support is in the collapsed configuration, and wherein the locking attachment is configured to engage the distal notch to maintain the piston in an advanced position wherein the support is in the expanded configuration.

6. The lens support system of claim 1, wherein the frame defines a first diameter in the collapsed configuration and a second diameter in the expanded configuration, the second diameter being greater than the first diameter.

7. The lens support system of claim 1, wherein frame has a diameter of between about 0.8 cm and about 1.6 cm in the expanded configuration.

8. The lens support system of claim 1, wherein the cannula is sized to be received through an incision in a pars plana of the patient having a length of between about 1 mm and 2 mm.

9. The lens support system of claim 1, wherein the cannula has a diameter of between about 0.4 mm and 0.6 mm.

* * * * *